United States Patent [19]

Kojima et al.

[11] Patent Number: 5,288,341
[45] Date of Patent: Feb. 22, 1994

[54] AGENT AND METHOD FOR TREATING THE SURFACES OF METALS

[75] Inventors: Katsunori Kojima, Tokyo; Yohji Imai, Chiba; Tetsuro Sakuma, Tokorozawa, all of Japan

[73] Assignee: GC Corporation, Tokyo, Japan

[21] Appl. No.: 943,676

[22] Filed: Sep. 11, 1992

[30] Foreign Application Priority Data

Oct. 30, 1991 [JP] Japan ................................. 3-10122

[51] Int. Cl.⁵ .............................................. A61K 6/00
[52] U.S. Cl. ..................... 148/248; 148/250; 156/315; 156/314; 156/316
[58] Field of Search .................... 156/315, 314, 316; 148/248, 250

[56] References Cited

U.S. PATENT DOCUMENTS

| | | | |
|---|---|---|---|
| 3,617,450 | 11/1971 | Kawasuchi | 204/12 |
| 3,654,021 | 4/1972 | Henkler | 156/331 |
| 4,185,052 | 1/1980 | Leber . | |
| 4,913,971 | 4/1990 | Beck | 428/424.8 |

FOREIGN PATENT DOCUMENTS 1341506 12/1973 United Kingdom .
1448970 9/1976 United Kingdom .

*Primary Examiner*—Sam Silverberg
*Attorney, Agent, or Firm*—Oblon, Spivak, McClelland, Maier & Neustadt

[57] ABSTRACT

An agent is characterized by containing a polymerizable monomer having a thiophosphoric acid dichloride group. By applying this agent to the surfaces of noble metals, much more durable and increased bond strength is obtained.

4 Claims, No Drawings

AGENT AND METHOD FOR TREATING THE SURFACES OF METALS

BACKGROUND OF THE INVENTION

The present invention relates generally to bonding together metals and, more particularly, to an agent and method for pre-treating the surfaces of the metals to be bonded together, when the metals are bonded together with the use of polymer adhesives.

As compared with bonding together base metals such as cobalt, chromium, nickel, titanium, iron and copper as well as their alloys, it is much more difficult to bond together chemically stable noble metals such as gold, platinum and palladium as well as noble metal alloys containing them as main components; that is, there is no or little technique to meet such demands.

In an effort to improve the adhesion of noble metals, applying primers on them, sandblasting their surfaces by physical means, tinning and oxidizing them have been proposed so far in the art. Of these procedures, the application of primers is the simplest one. Typical primers comprise monomers containing 6-(4-vinylbenzyl-n-propyl)amino-1,3,5-triazine-2,4-dithion (VBATDT), as set forth in Japanese Patent Application Laid-Open No. 64-83254 and thiophosphoric acid, as referred to in Japanese Patent Application Laid-Open No. 1-138282.

Some of the procedures mentioned above are found to be effective under dry conditions, but have the disadvantage of being poor in water resistance and durability. The application of primers, on the other hand, is considered preferable because of being free from such problems.

However, problems with using VBATDT as a primer are that some limitation is placed on what metals are bonded together and what catalysts are used for curing the bonding agent as well. It is admitted that the procedure of using a monomer containing a thiophosphoric acid group has some effect, but it offers storing and handling problems because the material is unstable.

A primary object of this invention is therefore to provide a pre-treatment or primer agent which can be used with every metal and every catalyst for curing adhesives and does not pose any storing and handling problems.

SUMMARY OF THE INVENTION

According to the present invention, the problem with using a thiophosphoric acid group-containing monomer can be solved, if a polymerizable monomer containing a thiophosphoric acid dichloride group that is the precursor thereof is used.

In other words, the present invention provides an agent for treating the surfaces of metals, in which 0.001 to 10% by weight of a thiophosphoric acid dichloride group-containing polymerizable monomer is dissolved in an organic solvent.

DETAILED DESCRIPTION OF THE INVENTION

The thiophosphoric acid dichloride group-containing polymerizable monomer used in this invention has the following general formula I or II:

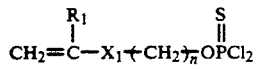
I

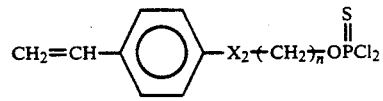
II where

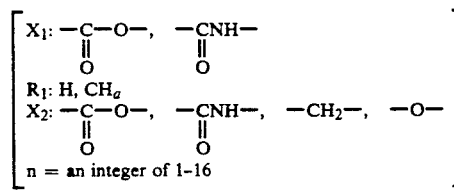

Set out below are preferable examples of the monomer according to this invention.

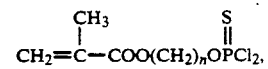

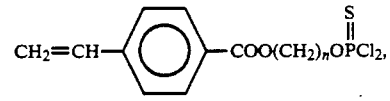

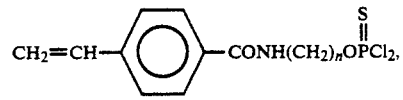

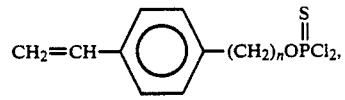

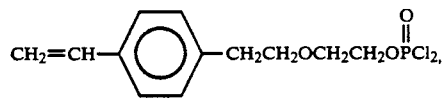

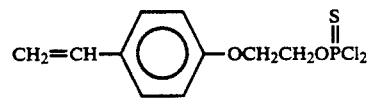

The thiophosphoric acid dichloride group-containing polymerizable monomer may be dissolved in an organic solvent at a concentration of 0.001 to 10% by weight. Used preferably to this end are acetone, methyl ethyl ketone, tetrahydrofuran, dioxane, ethyl acetate, methyl methacrylate, chloroform, benzene, toluene or their mixtures.

The thiophosphoric acid dichloride group-containing polymerizable monomer may be used by itself. If desired, it may be used in the form of a composition which is obtained by dissolving it in the organic solvent, followed by addition of water and a tertiary amine, each in an amount of 2 molar equivalents per monomer. The tertiary amine used to this end, for instance, may be triethylamine, tripropylamine, tributylamine and pyridine.

The concentration of the polymerizable monomer of this invention in the organic solvent may lie in the range of 0.001 to 10% by weight, preferably 0.01 to 5% by weight, although varing depending upon how to treat metals. To be more specific, a solution having a concentration as low as about 0.01 to 0.3% by weight may be applied on the surfaces of metals, or alternatively the metals may be immersed in that solution. Then, the solvent is evaporated off for direct bonding. In the case of using solutions having higher concentrations, excessive portions thereof should be well wiped off or washed off after applied on metals.

Irrespective of whether the treating solutions are low or high in concentration, it is generally preferred that washing be done so as to improve the adhesion between metals. Preferable washing solvents used, for instance, may be organic solvents such as methanol, ethanol, isopropanol, acetone, methyl ethyl ketone, tetrahydrofuran, chloroform, methylene chloride, ethyl acetate and methyl methacrylate or their mixtures.

A curing-by-polymerization type adhesive containing a polymerizable monomer having a double bond and a polymerization initiator as components is then applied on the thus pre-treated surface of the metal. Examples of the monomer are methyl methacrylate, 2-hydroxyethyl methacrylate, triethylene glycol methacrylate and 2,2-bis[4-(3-methacryloyloxy-2-hydroxypropoxy)-phenyl]propane (BIS-GMA). As the polymerization initiator, by way of example alone, 5-butyl-barbituric acid or 1-cyclohexyl-5-ethylbarbituric acid/copper chloride may be used. The metals to which this invention is applied, for instance, may be noble and base ones such as gold, platinum, silver, palladium, titanium, iron, tin, zinc and copper as well as their alloys.

EXAMPLES

This invention will now be explained more specifically but not exclusively with reference to the examples.

Example 1

Metal columns of 6–10 mm in diameter and 3–6.5 mm in height are used as test pieces. They were polished with silicon carbide polishing paper and then polished to finish with Imperial Lapping Felm #4000.

Next, 10-methacryloyloxydecyl thiophosphoric acid dichloride was synthesized and dissolved in acetone at a 5% concentration. This solution was used (A) by itself, (B) with water and triethylamine, each in one molar equivalent and (C) with water and triethylamine, each in two molar equivalents—Treating Solutions (A), (B) and (C). The treating solution was brushed on the surface of each test piece, which was in turn allowed to stand alone for 10 minutes for air drying. Thereafter, it was immersed in acetone for 30 minutes to 19 hours, and then removed therefrom, washed with acetone and air-dried to prepare the sample to be bonded.

For bonding testing, a set of two samples of the same metal were used. A cellophane tape having a hole of 5 mm in diameter was applied on the surface of one sample to measure coverage. Subsequently, a paste made up of polymethyl methacrylate containing 10% of tributylborane partial oxide (TBBO) was placed on the tape, to which the other sample treated on the surface was bonded under pressure. The thus bonded samples were let stand alone in the air of 37° C. for one day and in the water of 37° C., and subjected to heat cycle testing 2000 times, in which they were alternately immersed in the waters of 4° C. and 60° C. for one minute. Thereafter, they were subjected to tensile testing at a rate of 2 mm/min. For estimation, five measurements were averaged.

Set out below are the results of tests with nine metals.

TABLE 1

Tensile strength of metals when bonded after coating with 5% treating solution followed by immersion in acetone (MPa)

Time of immersion in acetone after coating with treating solutions (A, B, C)

| | 0.5 hr | 1.0 hr | | 3.0 hr | | | 19.0 hr | | |
|---|---|---|---|---|---|---|---|---|---|
| Metal | B | B | C | A | B | C | A | B | C |
| Au alloy | 26.7 | 28.3 | 18.8 | 24.4 | 26.3 | 26.5 | 13.4 | 31.9 | 41.2 |
| Au/Ag/Pd alloy | 38.9 | 32.7 | 37.0 | 43.0 | 24.7 | 32.1 | 40.9 | 23.8 | 45.3 |
| Ag alloy | 24.7 | 32.9 | 37.1 | 44.3 | 38.7 | 37.8 | 40.7 | 38.5 | 45.2 |
| Ni/cr alloy | 34.3 | 48.6 | 51.2 | 29.5 | 49.1 | 46.7 | 39.4 | 48.6 | 46.2 |
| Co/Cr alloy | 30.5 | 35.5 | 46.7 | 37.3 | 38.8 | 39.8 | 51.3 | 41.2 | 50.4 |
| Pt | 11.8 | 21.3 | 28.6 | 27.4 | 33.3 | 41.3 | 25.5 | 49.3 | 53.5 |
| Pd | 4.0 | 29.7 | 25.4 | 44.3 | 35.1 | 41.8 | 42.0 | 44.0 | 50.3 |
| Ag | 36.1 | 44.5 | 28.7 | 44.1 | 39.1 | 34.6 | 19.5 | 31.5 | 42.4 |
| Au | 5.6 | 9.0 | 4.8 | 9.6 | 6.2 | 17.7 | 3.2 | 4.5 | 9.6 |

Treating Solutions (A), (B) and (C) are all effective, but when they are used at a 5% concentration, it is not desirable that they are let stand alone in the air after coating; in other words, it is preferred that excess solutions are removed by immersion in acetone or the like.

Example 2

The procedures of Example 1 were followed with the exception that a 0.02% solution of Treating Solution (C) in acetone was used and the samples were immersed in acetone for 19 hours or let stand alone in the air for 19 hours after coating. The results are given in Table 2.

TABLE 2

Tensile bond strength (in MPa) between the samples immersed in acetone or let stand alone in the air for 19 hours, ten minutes after coating of a 0.02% solution of Treating Solution (C) in acetone

| Metal | immersion in acetone | standing in the air |
|---|---|---|
| Au alloy | 42.3 | 23.2 |
| Au/Ag/Pd alloy | 49.8 | 43.3 |
| Ag alloy | 46.6 | 39.3 |
| Ni/Cr alloy | 44.1 | 30.1 |
| Co/Cr alloy | 58.9 | 50.2 |
| Pt | 47.1 | 43.3 |

TABLE 2-continued

Tensile bond strength (in MPa) between the samples immersed in acetone or let stand alone in the air for 19 hours, ten minutes after coating of a 0.02% solution of Treating Solution (C) in acetone

| Metal | immersion in acetone | standing in the air |
|---|---|---|
| Pd | 50.3 | 42.2 |
| Ag | 52.3 | 49.4 |
| Au | 18.7 | 22.0 |

At a concentration as low as 0.02%, it has turned out that some considerable bond strength is obtained after let stand alone following coating without recourse to immersion in acetone. Still, it is desired that the metals be immersed in an organic solvent. Thus, whether or not the metals are immersed in an organic solvent may be determined depending upon what purpose they are used for.

Comparative Example 1

The procedures of Example 1 were followed with the exception that the test pieces were not subjected to any surface treatment. The results are reported in Table 3.

TABLE 3

Tensile bond strength (in MPa) between metals

| Metal | Comparative Example 1 (No Treatments) | Comparative Example 2 (Treatment with 4META) |
|---|---|---|
| Au alloy | 12.0 | 15.1 |
| Au/Ag/Pd alloy | 5.5 | 19.5 |
| Ag alloy | 16.2 | 3.1 |
| Ni/Cr alloy | 0 | 45.2 |
| Co/Cr alloy | 3.3 | 39.4 |
| Pt | 0 | 10.2 |
| Pd | 0 | 7.7 |
| Ag | 0 | 6.4 |
| Au | 0 | 3.4 |

Comparative Example 2

The procedures of Example 1 were followed with the exception that 4-methacryloyloxyethoxycarbonyl phthalic anhydride (4-META) said to be effective for bonding metals together was used in place of the surface treating solutions used there. The results are summarized in Table 3.

Example 3

The procedures of Example 1 were followed with the exception that two metals were bonded to an acrylic rod over a coverage of 3 mm in diameter with the use of a 1% solution of Treating Solution (C) and by immersion in acetone for 19 hours. The results are reported in Table 4. As will be understood from Table 4, the polymerization initiators used were TBBO, benzoyl peroxide/p-tolyldiethanolamine (BPO/TDEA) and 1-cyclohexyl-5-ethylbarbituric acid/copper chloride.

TABLE 4

Tensile bond strength (in MPa) between metals and acrylic rods

| Metal | TBBO | BPO/TDEA | Barbituric acid |
|---|---|---|---|
| Au alloy | 23.1 | 21.3 | 28.7 |
| Au/Ag/Pd alloy | 22.7 | 18.6 | 21.5 |

The present method is effective for every metal, and is particularly suitable for bonding together noble metals which are bonded together with some difficulty in conventional manners. With no need of relying upon troublesome procedures such as tinning and oxidization treatments, much more durable and increased bond strength is achievable by a simple procedure for which only coating is needed.

Problems with the thiophosphoric acid group-containing monomer is that it cannot in fact be obtained in pure form and it precipitates out when stored in solution form. By contrast, the thiophosphoric acid dichloride according to this invention can be isolated in pure form and stored as such; that is, it can be used in solution or composition form depending upon the type of metal, as occasion arises.

What is claimed is:

1. A method for treating the surface of a metal, comprising applying on the surface of a metal an agent comprising a polymerizable monomer comprising 0.001 to 10% by weight of a thiophosphoric acid dichloride group of the formula (I) or (II):

$$CH_2=\underset{R_1}{C}-X_1\text{+}CH_2\text{)}_n\overset{S}{\underset{\|}{O}}PCl_2, \quad (I)$$

or $$CH_2=CH-\text{\textlangle}\bigcirc\text{\textrangle}-X_2\text{+}CH_2\text{)}_n\overset{S}{\underset{\|}{O}}PCl_2, \quad (II)$$

wherein

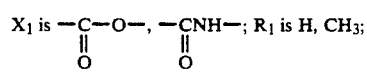

$R_1$ is H, $CH_3$;

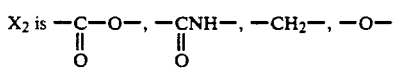

n is an integer of from 1–16, wherein said agent is dissolved in an organic solvent.

2. The method according to claim 1, wherein said method further comprises the step of removing excess agent.

3. The method according to claim 1, wherein said agent further comprises of water and 2 molar equivalents or less, based on said polymerizable monomer, of tertiary amine.

4. The method according to claim 3, wherein said method further comprises removing excess agent.

* * * * *